United States Patent [19]

Sung et al.

[11] Patent Number: 4,501,595

[45] Date of Patent: Feb. 26, 1985

[54] MIDDLE DISTILLATE FUEL OIL OF IMPROVED STORAGE STABILITY CONTAINING CONDENSATE OF MANNICH BASE AND ALKENYL SUCCINIC ACID ANHYDRIDE

[75] Inventors: Rodney L. Sung, Fishkill; Thomas J. Karol, Wappingers Falls, both of N.Y.

[73] Assignee: Texaco Inc., White Plains, N.Y.

[21] Appl. No.: 613,925

[22] Filed: May 25, 1984

[51] Int. Cl.³ .................................................. C10L 1/18
[52] U.S. Cl. ............................................ 44/57; 44/74; 44/75; 44/73; 44/64; 252/396

[58] Field of Search ................. 44/75, 74, 70, 57, 64, 44/73; 252/396

[56] References Cited

U.S. PATENT DOCUMENTS 3,944,397 3/1976 Gardiner et al. ...................... 44/74
4,398,921 8/1983 Rifkin et al. ........................... 44/75

Primary Examiner—Y. Harris-Smith
Attorney, Agent, or Firm—Robert A. Kulason; James J. O'Loughlin; Carl G. Seutter

[57] ABSTRACT

Diesel oil of improved storage stability contains condensate of tetraethylenepentamine; paraformaldehyde; 2,6-di-t-butyl phenol; and polyisobutenyl succinic acid anhydride.

14 Claims, No Drawings

MIDDLE DISTILLATE FUEL OIL OF IMPROVED STORAGE STABILITY CONTAINING CONDENSATE OF MANNICH BASE AND ALKENYL SUCCINIC ACID ANHYDRIDE

FIELD OF THE INVENTION

This invention relates to middle distillate fuel oils. More particularly it relates to middle distillate fuel oils characterized by improved storage stability.

BACKGROUND OF THE INVENTION

As is well known to those skilled in the art, middle distillate fuels typified by diesel fuel, home heating oil, etc are characterized by undesirable storage stability when stored in the presence of air even at room temperature. Over the course of time, these fuels become cloudy and produce sediment which deposits on the surfaces with which the fuel comes into contact. It particularly deposits on and clogs small openings such as those in fuel filters and strainers, in diesel engine injection nozzles, etc. It is an object of this invention to provide a middle distillate fuel oil characterized by improved storage stability. Other objects will be apparent to those skilled in the art.

STATEMENT OF THE INVENTION

In accordance with certain of its aspects, this invention is directed to a middle distillate fuel oil composition characterized by improved storage stability which comprises a major portion of a middle distillate fuel oil; and a minor stability-improving amount of an additive prepared by reacting (i) a primary or secondary polyamine, (ii) an aldehyde, and (iii) a phenol containing an active hydrogen thereby forming a phenol-aldehyde-amine condensate;

reacting said phenol-aldehyde-amine condensate with (iv) a succinic acid anhydride bearing a polyolefin-derived substituent containing residual unsaturation thereby forming product phenol-aldehyde-amine Mannich condensate polyamine succinimide; and recovering said product phenol-aldehyde-amine Mannich condensate polyamine succinimide.

DESCRIPTION OF THE INVENTION

The charge compositions which may be employed in practice of the process of this invention according to certain of its aspects may include primary amines or secondary amines. The amines may typically be characterized by the formula

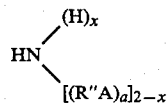

wherein R" is a divalent hydrocarbon group preferably a lower ($C_1$-$C_{10}$) alkylene group. A may be —OH or —N(R')$_2$. a may be 1-20, preferably 1-10, say 5. x may be 0 or 1.

In the above compound, R' may be hydrogen or a hydrocarbon radical selected from the group consisting of alkyl, aralkyl, cycloakyl, aryl, alkaryl, alkenyl, and alkynyl including such radicals when inertly substituted. When R' is alkyl, it may typically be methyl, ethyl, n-propyl, iso-propyl, n-butyl, i-butyl, sec-butyl, amyl, octyl, decyl, octadecyl, etc. When R' is aralkyl, it may typically be benzyl, beta-phenylethyl, etc. When R' is cycloalkyl, it may typically be cyclohexyl, cycloheptyl, cyclooctyl, 2-methylcyclo-heptyl, 3-butylcyclohexyl, 3-methylcyclohexyl, etc. When R' is aryl, it may typically be phenyl, naphthyl, etc. When R' is alkaryl, it may typically be tolyl, xylyl, etc. When R' is alkenyl, it may typically be vinyl, allyl, 1-butenyl, etc. When R' is alkynyl, it may typically be ethynyl, propynyl, butynyl, etc. R' may be inertly substituted i.e. it may bear a non-reactive substituent such as alkyl, aryl, cycloalkyl, ether, halogen, nitro, etc. Typically inertly substituted R' groups may include 3-chloropropyl, 2-ethoxyethyl, carboethoxymethyl, 4-methyl cyclohexyl, p-chlorpheny, p-chlorobenzyl, 3-chloro-5-methylphenyl, etc. The preferred R' groups may be hydrogen or lower alkyl, i.e. $C_1$-$C_{10}$ alkyl, groups including eg methyl, ethyl, n-propyl, i-propyl, butyls, amyls, hexyls, octyls, decyls, etc. R' may preferably be hydrogen.

R" may be selected from the same group as R' subject to the fact that R" is divalent and contains one less hydrogen. Preferably R' is hydrogen and R" is —$CH_2CH_2$—. Typical amines which may be employed may include the following.

| TABLE |
|---|
| propylenediamine |
| diethylenetriamine |
| di-isopropylenetriamine |
| triethylenetetramine |
| tetraethylenepentamine |
| pentaethylenehexamine, etc. |

The preferred amine may be tetraethylenepentamine.

The charge aldehyde which may be employed may include those preferably characterized by the formula $R^2$ CHO.

In the above compound, $R^2$ may be hydrogen or a hydrocarbon radical selected from the group consisting of alkyl, aralkyl, cycloalkyl, aryl, alkaryl, alkenyl, and alkynyl including such radicals when inertly substituted. When $R^2$ is alkyl, it may typically be methyl, ethyl, n-propyl, iso-propyl, n-butyl, i-butyl, sec-butyl, amyl, octyl, decyl, octadecyl, etc. When $R^2$ is aralkyl, it may typically be benzyl, beta-phenylethyl, etc. When $R^2$ is cycloalkyl, it may typically be cyclohexyl, cycloheptyl, cyclooctyl, 2-methylcycloheptyl, 3-butylcyclohexyl, 3-methylcyclohexyl, etc. When $R^2$ is aryl, it may typically be phenyl, naphthyl, etc. When $R^2$ is alkaryl, it may typically be tolyl, xylyl, etc. When $R^2$ is alkenyl, it may typically be vinyl, allyl, 1-butenyl, etc. When $R^2$ is alkynyl, it may typically be ethynyl, propynyl, butynyl, etc. $R^2$ may be inertly substituted i.e. it may bear a non-reactive substituent such as alkyl, aryl, cycloalkyl, ether, halogen, nitro, etc. Typically inertly substituted R groups may include 3-chloropropyl, 2-ethoxyethyl, carboethyoxymethyl, 4-methylcyclohexyl, p-chlorphenyl, p-chlorobenzyl, 3-chloro-5-methylphenyl, etc. The preferred $R^2$ groups may be lower alkyl, i.e. $C_1$-$C_{10}$ alkyl, groups including eg methyl, ethyl, n-propyl, i-propyl, butyls, amyls, hexyls, octyls, decyls, etc. $R^2$ may preferably be hydrogen.

Typical aldehydes which may be employed may include the following:

| TABLE |
|---|
| formaldehyde |
| ethanal |
| propanal |

TABLE-continued butanal

The preferred aldehyde may be formaldehyde employed as its polymer-paraformaldehyde.

The charge phenols which may be employed in practice of the process of this invention may preferably be characterized by the formula $HR^3OH$. It is a feature of these phenols that they contain at least one active hydrogen which can react with the aldehyde moiety. Poly-phenols (eg compounds containing more than one hydroxy group in the molecule whether on the same ring or not) may be employed. The rings on which the hydroxy groups are sited may bear inert substituents. However at least one position (which may be meta- but which is preferably ortho or para- to a phenol hydroxy group) must be occupied by an active hydrogen as this is the point of reaction with the aldehyde group.

$R^3$ may be an arylene group typified by $-C_6H_4-$, $-C_6H_3(CH_3)-$, $-C_6H_3(C_2H_5)-$, etc.

Typical phenols which may be employed may include:

TABLE phenol
2,6-di-t-butyl phenol
beta-naphthol
resorcinol
bis-4,4-(2,6-di-t-butyl phenol) methane
catechol The preferred phenol may be 2,6-di-t-butylphenol.

Reaction to form the phenol-amine-aldehyde Mannich condensate may be effected by adding 0.8–1.5 moles, say 1 mole of aldehyde and 0.8–1.2 moles, say 1 mole of amine and 0.8–1.2 moles, say 1 mole of phenol. In one preferred embodiment, one mole of paraformaldehyde may react with one mole of 2,6-di-t-butyl phenol and 1 mole of tetraethylene pentamine.

Reaction is preferably effected by adding the reactants (preferably the aldehyde is added last) to a reaction operation under a blanket of inert gas, typically nitrogen. The reaction mixture is maintained at 80° C.–160° C., say about reflux temperature of about 100° C. for 0.5–5 hours, say 2 hours. By-product water distills off.

Typically reaction may be as follows:

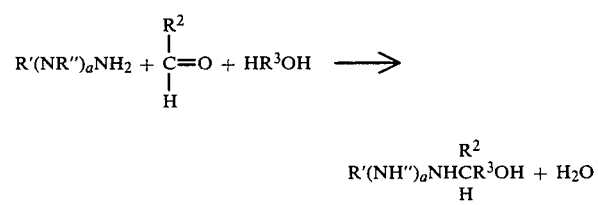

In a specific embodiment, the reaction may be as follows:

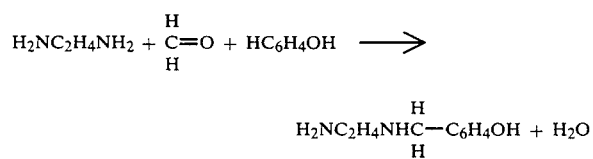

Illustrative phenol-amine-aldehyde Mannich base condensates which may be so formed include the following:

TABLE

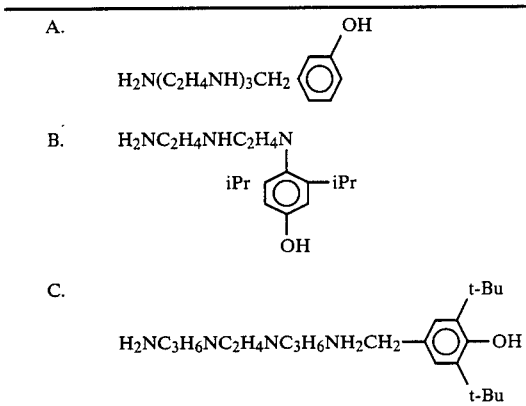

At the conclusion of the reaction, the Mannich condensate product may be further reacted in situ although preferably it is filtered hot.

In practice of the process of this invention, the Mannich condensate may thereafter be reacted with a succinic acid anhydride bearing a polyolefin substituent containing residual unsaturation; in one preferred embodiment, all the reactants may be simultaneously reacted (including succinic acid anhydride bearing a polyolefin substituent containing residual unsaturation) in a "one pot" reaction.

The succinic acid anhydride may be characterized by the following formula

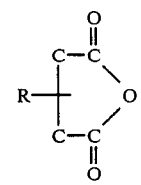

In the above formula, R may be a residue (containing residual unsaturation) from a polyolefin which was reacted with maleic acid anhydride to form the alkenyl succinic acid anhydride. R may have a molecular weight $\overline{M}_n$ of 500–2000, preferably 1000–1300, say about 1300.

Reaction is preferably carried out by adding 0.5–1 mole, say 1 mole of the phenol-aldehyde-amine Mannich base condensate and 0.9–1.1 moles, say 1 mole of the alkenyl succinic acid anhydride.

Reaction is preferably carried out in the presence of inert diluent-solvent typified by a heavy hydrocarbon. A preferred diluent-solvent is a hydrocarbon of lubricating oil character—preferably the lubricating oil in which the product is to be used. A more preferred diluent-solvent is the 100 E Pale Stock HF oil. The diluent-solvent is preferably present in amount of 0–5 w%, say 50 w% parts of the other components of the reaction mixture.

Reaction is preferably carried out by adding the diluent-solvent oil and the phenol-aldehyde-amine condensate to the reaction vessel. Preferably the reaction is carried out under a blanket of inert gas such as nitrogen. The reaction mixture may be heated to 30° C.–120° C., say 60° C. and the alkenyl succinic acid anhydride is added with agitation. The mixture is heated to 100° C.-160° C., say 110° C.-120° C. for 1-6 hours, say 2 hours and then filtered hot.

In a preferred embodiment, reaction may be carried out by forming the phenol-aldehyde-amine Mannich condensate in situ. The several charge materials may be added to the reaction system viz the phenol, aldehyde, amine, anhydride, and diluent-solvent oil. The reaction mixture may be heated at 100° C.-160° C., say 115° C. for 1-6 hours, say 2 hours and then filtered hot.

The product so obtained is a 50-100 w%, say 50 w% solution in inert diluent of the desired additive; and preferably it is used in this form.

The typical reaction may be as follows:

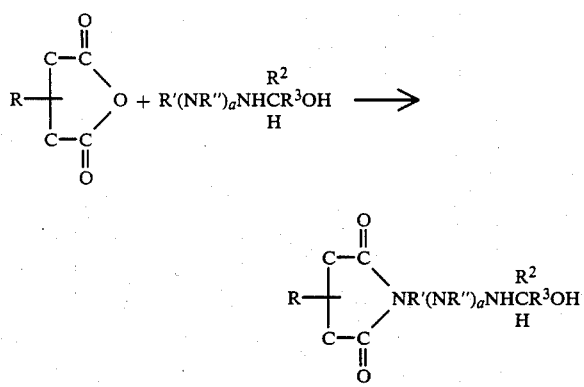

In a specific preferred embodiment, the reaction may be as follows:

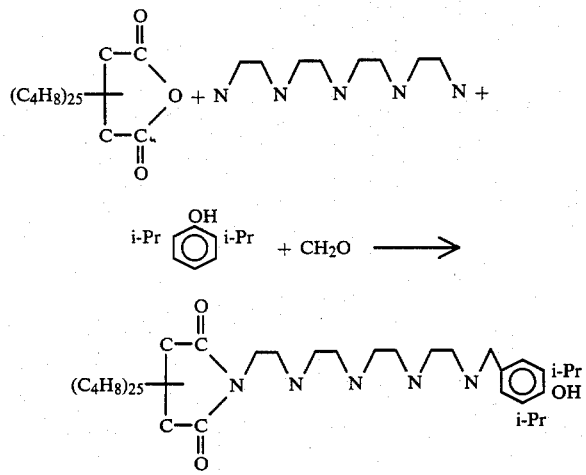

The middle distillate fuel oil compositions to which these products may be added include hydrocarbon liquids having an ibp of 300° F.-430° F., say about 400° F., a 50% bp of 430° F.-600° F., say 517° F., a 90% bp of 500° F.-650° F., say 597° F. and an API gravity of 30-40, say 35.2. They may be commonly indentified as kerosene, Avjet fuel, diesel oil, fuel oil, home heating oil, etc. They include products having the noted boiling points recovered as cuts from oils obtained by the hydrogenation of heavy oils or of solid carbonaceous fuels such as coal typified by the liquid identified as diesel fuel cut from H-oil.

It is a feature of this invention that improved storage stability may be imparted to middle distillate fuel oils by addition thereto of a stability-improving amount of the above-noted additive. A stability-improving amount may be 0.25-250 PTB, preferably 10-100 PTB, say 25 PTB. (PTB stands for pounds per thousand barrels). This corresponds to 0.0001-0.1 w%, preferably 0.04-0.004 w%, say 0.01 w%.

Presence of effective amount of additive imparts improved storage stability as measured by the Potential Deposit Test (PDT). In this test, a rating of 1 or 2 are good; ratings of 3 or 4 are failing.

The Potential Deposit Test procedure requires filtering of 100 ml of the test fuel into a test tube through a 15 centimeter Number 1 Whatman filter paper. An air delivery tube was inserted in the test tube through a cork that has been slotted on the sides to allow the air to escape. The delivery tube was adjusted so that its tip which has been cut at a 45 degree angle, just touches the bottom of the test tube. The test tube was placed in an oil bath of 270±1° F. and preheated. The delivery tube was connected to a flow meter and air was bubbled through the fuel for 2 hours at a rate of 3 liters per hour. To remove acidic materials from the air, the air was first bubbled through 20% caustic solution, and then bubbled through distilled water prior to passing it through the test fuel. The test tube was removed from the oil bath, the oil was wiped from the outside of the tube and the tube was placed in a constant temperature bath maintained at 77±0.5° F. The test fuel sample was then filtered using suction at pressure of 75 to 85 mm Hg below atmospheric pressure through a 4.25 cm. No. 1 Whatman filter paper clamped between two halves of Millipore filter holder. The fuel oil from the funnel and filter paper was washed with three, 5 ml portions of n-heptane. The filter paper disk was removed and compared visually with those on the Potential Deposit Code.

The Base Fuel employed in the Potential Deposit Test was a mineral oil processed by conventional refining methods and having the following characteristics:

| Gravity, API | 35.2 |
| --- | --- |
| Kinetic Viscosity, 100° F., cs | 2.86 |
| Flash Point, ° F. | 162 |
| Pour Point, ° F. | +5 |
| Cloud Point, ° F. | +4 |
| ASTM Distillation: | |
| Initial boiling point | 400° F. |
| 10% distilled at | 426° F. |
| 30% distilled at | 479° F. |
| 50% distilled at | 517° F. |
| 70% distilled at | 554° F. |
| 90% distilled at | 597° F. |
| 95% distilled at | 615° F. |
| Final Boiling Point | 628° F. |

It is found that the middle distillate fuel compositions containing effective amounts of additive receive favorable (1 or 2) ratings on the test. These ratings correlate with practical observation of decreased deposits in bodies of middle distillate fuel.

DESCRIPTION OF SPECIFIC EMBODIMENTS

Practice of the process of this invention may be apparent to those skilled in the art from the following wherein, as elsewhere in this specification, all parts are parts by weight unless otherwise specified.

EXAMPLE I

In this example which represents the best mode presently known, the following reactants were employed:

TABLE

| Reactant | Grams | Moles |
|---|---|---|
| 1. Tetraethylenepentamine | 100 | 0.53 |
| 2. 2,6,-di-t-butyl phenol | 109.0 | 0.53 |
| 3. Para formaldehyde | 24 | 0.80 |
| 4. Poly isobutenyl ($\overline{M}_n$ 1290) succinic acid anhydride-Sap. No. 51.9 as a 5.9 w % solution in 100 E Pale Stock HF | 410 | 0.189 |
| 5. 100 E Pale Stock HF diluent oil | 413 | — |

The amine, the phenol, and the aldehyde were charged in that order to a reaction vessel under a blanket of nitrogen. The reaction mixture, under a blanket of nitrogen, was refluxed at ca. 100° C. for 2 hours and vacuum filtered hot.

52.3 grams (0.124 moles) of the phenol-amine Mannich condensate so prepared were added to a reaction vessel together with the Pale Stock diluent-solvent. Under a nitrogen blanket, the reaction mixture was heated to 60° C. and the anhydride (in solution of oil) was added with stirring. The reaction mixture was heated to 110° C.–120° C. under reflux over 2 hours. The product was filtered hot.

EXAMPLE II

In this example, the following reactants were employed:

| Reactants | Parts | Moles |
|---|---|---|
| 1. The phenol-amine-aldehyde condensate of Example I | 70 | 0.167 |
| 2. Polyisobutenyl ($\overline{M}_n$ 1290) succinic acid anhydride-Sap No 51.9 as a 5.9 w % solution in 100 E Pale Stock HF | 400 | 0.185 |
| 3. 100 E Pale Stock HF diluent oil | 420 | — |

The procedure of paragraphs 2-3 of Example I was followed.

EXAMPLES III-IV-V

In the Examples which follow, tests were made on the Base Oil set forth above in the description of the Potential Deposit Test.

EXAMPLES III-IV-V

In these Examples, the additives of Examples I-II were added to the noted Base Oil in amount of 25 PTB and the resultant composition was tested in the Potential Deposit Test.

TEST

| Example | Additive | PTB | Rating |
|---|---|---|---|
| III | none | — | 3 |
| IV | Example I | 25 | 2 |
| V | Example II | 25 | 2 |

From the above table, it is apparent that the Base Oil above has an unsatisfactory rating of 3, and the composition containing Base Oil plus 25 PTB of additive has a satisfactory rating of 2.

EXAMPLE VI

In this example, the Base Oil is a diesel fuel having the following characteristics:

TABLE

BASE OIL

| | |
|---|---|
| Flash Point, ° F. CM | 280 |
| Cloud Point, ° F. | +5 |
| Pour Point, ° F. | 0 |
| Kin. Vis cs @ 40° F. | 4.3 |
| Cetane | 50.6 |
| FIA Analysis | |
| A % | 35.5 |
| O % | 12.5 |
| S % | 52.0 |
| S % | 0.41 |
| Con. Cu strip 3 hrs. 122° F. | 1A |
| API Gravity | 31.4 |
| ASTM Distillation, °F. | |
| IBP | 540 |
| 10% | 546 |
| 30% | 561 |
| 50% | 566 |
| 70% | 572 |
| 90% | 582 |
| EP | 593 |

When tested in the PDT, this fuel received a rating of 4+. Addition of 100 PTB of the additive of Example I bettered the rating to 1.

EXAMPLES VII-X

Results comparable to those of Example VI may be attained by adding 100 PTB of the additives of Example 1 to the following middle distillate fuels:

| EXAMPLE | FUEL |
|---|---|
| VII | home heating oil |
| VIII | kerosene |
| IX | gas oil |
| X | light cycle gas oil |

EXAMPLES XI-XII-XIII

In this Example XI, the Base Oil is a standard D-2 Diesel Oil. The additive is prepared by the reaction of equal molar portions of 2,6-di-t-butylphenol; formaldehyde; and the polyisobutenyl ($\overline{M}_n$ 1290) succinimide of tetraethylenepentamine. The additive is present in amount of 100 PTB.

In Example XII, the additive is comparable except that the amine is pentaethylenehexamine.

In Control Example XIII, there is no additive present.

The Ratings on the Potential Deposit Test are as follows:

TABLE

| Example | Rating |
|---|---|
| XI | 1 |
| XII | 1 |
| XIII | 5+ |

Although this invention has been illustrated by reference to specific embodiments, it will be apparent to those skilled in the art that various changes and modifications may be made which clearly fall within the scope of this invention.

What is claimed is:

1. A middle distillate fuel oil composition characterized by improved storage stability which comprises
a major portion of a middle distillate fuel oil; and
a minor stability-improving amount of an additive prepared by reacting (i) a primary or secondary polyamine, (ii) an aldehyde, and (iii) a phenol containing an active hydrogen thereby forming a phenol-aldehyde-amine condensate;
reacting said phenol-aldehyde-amine condensate with (iv) a succinic acid anhydride bearing a polyolefin-derived substituent containing residual unsaturation thereby forming product phenol-aldehyde-amine Mannich condensate polyamine succinimide; and
recovering said product phenol-aldehyde-amine Mannich condensate polyamine succinimide.

2. A middle distillate fuel oil composition as claimed in claim 1 wherein said polyamine is a primary amine $(R')_2(NR'')_aNH_2$ wherein a is 1-10, R' is a hydrogen group selected from the group consisting of alkyl, alkaryl, aralkyl, cycloalkyl, alkenyl, alkynyl, and aryl and R'' is a divalent hydrocarbon selected from the same group as R' and containing one less hydrogen atom.

3. A middle distillate fuel oil composition as claimed in claim 1 wherein said polyamine is tetraethylenepentamine.

4. A middle distillate fuel oil composition as claimed in claim 1 wherein said polyamine is pentaethylenehexamine.

5. A middle distillate fuel oil composition as claimed in claim 1 wherein said polyamine is a secondary amine $[R'(NR'')_a]_2NH$.

6. A middle distillate fuel oil composition as claimed in claim 1 wherein said aldehyde is paraformaldehyde.

7. A middle distillate fuel oil composition as claimed in claim 1 wherein said phenol is 2,6-di-t-butylphenol.

8. A middle distillate fuel oil composition as claimed in claim 1 wherein said phenol is bis-4,4-(2,6-di-t-butylphenol).

9. A middle distillate fuel oil composition as claimed in claim 1 wherein said stability-improving amount is 0.25-250 PTB.

10. A middle distillate fuel oil composition as claimed in claim 1 wherein said stability-improving amount is 10-100 PTB.

11. A middle distillate fuel oil composition as claimed in claim 1 wherein said middle distillate fuel oil is a diesel fuel oil.

12. A middle distillate fuel oil composition as claimed in claim 1 wherein said middle distillate fuel oil is a diesel fuel oil fraction from the hydrogenation of solid carbonaceous fuel.

13. A diesel fuel oil composition characterized by improved storage stability which comprises
a major portion of a diesel fuel oil; and
a minor stability-improving amount of 0.25-250 PTB of an additive prepared by
reacting tetraethylenepentamine; paraformaldehyde; 2,6-di-t-butyl phenol; and polyisobutenyl succinic acid anhydride.

14. The method of treating a middle distillate fuel oil to impart thereto improved storage stability which comprises
adding to a middle distillate fuel oil a stability improving amount of an additive prepared by
reacting (i) a primary or secondary polyamine, (ii) an aldehyde, and (iii) a phenol containing an active hydrogen thereby froming a phenol-aldehyde-amine condensate;
reacting said phenol-aldehyde-amine condensate with (iv) a succinic acid anhydride bearing a polyolefin-derived substituent containing residual unsaturation thereby forming product phenol-aldehyde-amine Mannich condensate polyamine succinimide; and
recovering said product
phenol-aldehyde-amine Mannich condensate polyamine succinimide.

* * * * *